(12) United States Patent
Pehratovic et al.

(10) Patent No.: US 10,660,836 B2
(45) Date of Patent: May 26, 2020

(54) HYDROXY FUNCTIONALIZED SOLVENT BASED SKIN BENEFIT COMPOSITION

(71) Applicant: Conopco, Inc., Englewood Cliffs, NJ (US)

(72) Inventors: Hasiba Pehratovic, New Britain, CT (US); Jennifer Lyn Craig, Naugatuck, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/064,112

(22) PCT Filed: Dec. 8, 2016

(86) PCT No.: PCT/EP2016/080320
§ 371 (c)(1),
(2) Date: Jun. 20, 2018

(87) PCT Pub. No.: WO2017/108438
PCT Pub. Date: Jun. 29, 2017

(65) Prior Publication Data
US 2018/0369092 A1 Dec. 27, 2018

(30) Foreign Application Priority Data

Dec. 22, 2015 (EP) .................................... 15201905

(51) Int. Cl.
| | | |
|---|---|---|
| *A61K 8/365* | (2006.01) | |
| *A61K 8/34* | (2006.01) | |
| *A61K 8/39* | (2006.01) | |
| *A61Q 19/02* | (2006.01) | |
| *A61Q 19/08* | (2006.01) | |
| *A61K 8/03* | (2006.01) | |
| *A61Q 19/00* | (2006.01) | |

(52) U.S. Cl.
CPC ................ *A61K 8/365* (2013.01); *A61K 8/03* (2013.01); *A61K 8/34* (2013.01); *A61K 8/345* (2013.01); *A61K 8/39* (2013.01); *A61Q 19/00* (2013.01); *A61Q 19/02* (2013.01); *A61Q 19/08* (2013.01); *A61K 2800/262* (2013.01)

(58) Field of Classification Search
CPC ...... A61K 2800/262; A61K 8/03; A61K 8/34; A61K 8/345; A61K 8/365; A61K 8/39
See application file for complete search history.

(56) References Cited

U.S. PATENT DOCUMENTS

| | | | |
|---|---|---|---|
| 5,137,714 A | 8/1992 | Scott | |
| 6,083,493 A | 4/2000 | Swaile | |
| 6,423,325 B1 | 7/2002 | Alaluf et al. | |
| 2005/0100572 A1* | 5/2005 | Hatajima | A61K 8/0229 424/401 |
| 2007/0259012 A1 | 11/2007 | Castro et al. | |
| 2009/0317341 A1 | 12/2009 | Madison | |
| 2011/0033404 A1 | 2/2011 | Madison | |
| 2012/0122936 A1* | 5/2012 | Madison | A61K 8/365 514/356 |

FOREIGN PATENT DOCUMENTS

| | | |
|---|---|---|
| EP | 2329808 | 6/2011 |
| JP | 2005089337 | 4/2005 |

OTHER PUBLICATIONS

IPRP2 in PCTEP2016080320; dated Mar. 16, 2018.
Search Report and Written Opinion in EP15201905; dated May 19, 2016.
Search Report and Written Opinion in PCTEP2016080320; dated Feb. 8, 2017.
Written Opinion 2 in PCTEP2016080320; dated Nov. 24, 2017.

* cited by examiner

*Primary Examiner* — Nannette Holloman
(74) *Attorney, Agent, or Firm* — Edward A. Squillante, Jr.

(57) ABSTRACT

Described is a skin benefit cosmetic composition having a functionalized solvent and 12-hydroxystearic acid. The composition is at least substantially transparent and yields excellent skin benefits when topically applied.

14 Claims, No Drawings

HYDROXY FUNCTIONALIZED SOLVENT BASED SKIN BENEFIT COMPOSITION

FIELD OF THE INVENTION

The present invention is directed to a skin benefit cosmetic composition. More particularly, the invention is directed to a cosmetic composition comprising a hydroxy functionalized solvent and 12-hydroxystearic acid. The cosmetic composition is substantially transparent (preferably transparent) and unexpectedly delivers excellent skin benefits to consumers while surprisingly remaining free of crystallization and gellation.

BACKGROUND OF THE INVENTION

Skin appearance is a major indicia of looking healthy. Skin color, the lack of wrinkles and a complexion free of blemishes certainly makes one look and feel better.

Make-up formulas, for example, have been designed to mimic a person's skin tones. High loadings of colorants are optical ingredients necessary for such formulae. While formulae loaded with colorants achieve a covering purpose, high levels of colorants can negatively interfere with sensory attributes and active deposition. In fact, high levels of colorant can make skin look artificial in nature.

Other formulae that provide benefits to skin rely on the soft focus effect and utilize metal oxides, like titanium dioxide. These formulas often whiten skin and hide blemishes but are easy to rub-off after application and usually result in an undesirable ashen appearance. Furthermore, such products are draggy, and therefore, provide little sensory benefits and are hard to apply and create a homogeneous complexion.

It is of increasing interest to develop compositions that are suitable to improve the look and feel of skin while simultaneously providing exceptional sensory and nourishing benefits to skin. This invention, therefore, is directed to a skin benefit composition for improving the appearance of skin. The composition is one comprising a hydroxy functionalized solvent and 12-hydroxystearic acid. The composition, surprisingly, is at least substantially transparent, free of crystallization and gellation and one which delivers excellent sensory, skin nourishing, anti-aging and/or lightening benefits to consumers. Also, the composition is one which generally improves the overall quality of skin.

ADDITIONAL INFORMATION

Effects have been disclosed for making topical compositions. In U.S. Pat. No. 5,137,714, anhydrous cosmetic compositions with stable lower alkyl esters of pyroglutamic acid are described.

Other efforts have been disclosed for making topical compositions. In U.S. Patent Application Nos. 2009/317341 and 2011/033404, compositions with 12-hydroxystearic acid are described.

Still other efforts have been disclosed for making topical compositions. In U.S. Pat. No. 6,423,325, topical skin care compositions are described.

None of the additional information describes a topical composition as claimed in this invention.

SUMMARY OF THE INVENTION

In a first aspect, the present invention is directed to a composition comprising:
(a) 12-hydroxystearic acid; and
(b) a hydroxy functionalized solvent,
the composition being substantially transparent and substantially free of water, and the hydroxy functionalized solvent has an HD content of greater than 0.03.

In a second aspect, the present invention is directed to the composition of the first aspect of this invention further comprising a co-solvent that is miscible with the hydroxy functionalized solvent.

In a third aspect, the present invention is directed to a method for treating skin with the composition of the first or second aspect of this invention.

In a fourth aspect, the present invention is directed to a double phase product comprising the composition of the first or second aspect of this invention packaged along with a separate and distinct phase comprising water, water soluble ingredients, or both.

All other aspects of the present invention will more readily become apparent upon considering the detailed description and examples which follow.

Cosmetic composition is meant to mean a leave-on or wash-off composition, preferably leave-on, for topical application to mammals, especially humans. Such a composition can include tonics, lotions, personal washes, serums, spot correctors, compositions for facial masks or wipes, make-up removers, patches, scrubs or the like. Substantially transparent as used herein, means allowing light to pass but diffusing the light so that items on the opposite side of light entry are not clearly visible. Substantially transparent is synonymous with translucent. Transparent, as used herein, means capable of transmitting light where objects opposite the point of entry of light are seen clearly upon a visable inspection (i.e., 2.5 cm of sample placed 5 cm over an object and viewed from 25 cm away from viewer's eyes). Flowable, as used herein, means having a viscosity from 0 to 8,000 cps, and preferably, from 10 to 4,000 cps, and most preferably, from 500 to 2,000 cps, including all ranges subsumed therein (viscosity measured on a Brookfield Viscometer, 24° C., 20 RPM, Spindle RV2). Free of crystallization and gelation as used herein means remaining at least substantially transparent (preferably transparent) at ambient temperature for at least three (3) months. Use of substantially transparent, transparent and translucent herein is based on the mixture of hydroxy functionalized solvent (with or without miscible co-solvent) and 12-hydroxystearic acid. It is not to say the mixture cannot, for example, comprise an optional opacifier. Hydroxy group density ("HD") means the molecular weight of total solvent hydroxy group/the molecular weight of the solvent where solvent hydroxy group can include the hydroxy group on a carboxylic acid group. Methanol, for example, has an HD of 0.53, 17 g/mol/32 g/mol. Regarding optional additives, they may be used according to their solubility where those that are not water soluble may be selected for use in the composition substantially free of water as described herein and those which are water soluble may be used in the aforementioned optional but separate and distinct phase. Miscible/Soluble, as used herein, means ability to mix/dissolve homogeneously at 70 to 85° C. and remain homogeneously dissolved or mixed upon cooling. Comprising, as used herein, is meant to include consisting essentially of and consisting of. For the avoidance of doubt, therefore, the composition of this invention may consist essentially of or consist of 12-hydroxystearic acid and hydroxy functionalized solvent. Anhydrous as used herein means a composition substantially free of water whereby the composition is less than 2% by weight water, and preferably, less than 1% by weight water based on total weight of the composition comprising 12-hydroxystearic acid and hydroxy functionalized solvent. Anhydrous also includes free of water (i.e., no water) within the composition comprising 12-hydroxystearic and hydroxy fuctionalized solvent. Double phase product includes a two (2) portion product that may be separately packaged or preferably a biphasic product (i.e., distinct immiscible portions). Skin benefit agent means an agent in addition to hydroxyl functionalized solvent and 12-hydroxystearic acid that provides benefit to skin. The skin benefit agent used in the anhydrous composition of the invention that comprises 12-hydroxystearic acid is preferably soluble or miscible in the same. To the extent optional water miscible/soluble actives or ingredients are used, they will preferably be provided, as later described, in a double phase product with the anhydrous composition of this invention, the double phase product having a distinct phase often being a water phase (including emulsions, solutions and dispersions), water containing concentrate or water soluble solid, particulate or powder. Water phase, as used herein, includes a composition having 2% or more water, and preferably, from 10% to 98% by weight water based on total weight of the water phase. Water phase also includes a composition which is a concentrate or solid with little to no water (i.e., 0.0 to 5.0% by weight water based on total weight of the composition) but that is soluble in water. In an embodiment of this invention, the separate and distinct phase when water comprising is substantially transparent or transparent as herein defined.

Except in the operating and comparative examples, or where otherwise explicitly indicated, all numbers in this description indicating amounts or ratios of materials or conditions or reaction, physical properties of materials and/or use are to be understood as modified by the word "about".

DETAILED DESCRIPTION OF THE INVENTION

The only limitations with respect to the hydroxy functionalized solvent that may be used in this invention are that the same has an HD greater than 0.03, is suitable for use in a topical composition and results in a composition that is substantially transparent, preferably transparent. Often, the HD of the solvent is greater than 0.03 to 0.8, and preferably, from 0.05 to 0.65, and most preferably, from 0.1 to 0.55, including all ranges subsumed therein.

In some embodiments, the hydroxy functionalized solvent is methanol, ethanol, benzyl alcohol 2-(2-ethoxyethoxy) ethanol, phenoxyethanol, pentylene glycol or a mixture thereof. In other embodiments, the functionalized solvent is pentylene glycol, ethanol, methanol or a mixture thereof.

The 12-hydroxystearic acid used in this invention is a preferred skin benefit agent within the anhydrous composition. The same may be used as the sole skin benefit agent in the composition along with the hydroxy functionalized solvent, or optionally, 12-hydroxystearic acid may be used with additional but optional skin benefit agents. The composition of the present invention when comprising, consisting essentially of or consisting of 12-hydroxystearic acid as the benefit agent surprisingly moistens skin, strengthens the stratum corneum, provides anti-aging benefits and/or lightens skin after topical application.

Typically, the skin benefit agent portion (i.e., benefit agent in the composition in addition to solvent) of the anhydrous composition of this invention will comprise at least twenty-five percent by weight 12-hydroxystearic acid based on total weight of the skin benefit agent. The skin benefit agent portion of the composition of this invention is typically from 25 to 100%, and preferably, from 35 to 98%, and most preferably, from 50 to 95% by weight 12-hydroxystearic acid based on total weight of the skin benefit agent and including all ranges subsumed therein.

The anhydrous composition of the present invention will typically comprise at least 0.0001 percent by weight, and preferably, from 0.01 to 20%, and most preferably, from 0.80 to 5% by weight 12-hydroxystearic acid based on total weight of the anhydrous composition and including all ranges subsumed therein.

In particular, a composition is preferred comprising:
(a) 0.01 to 5, more preferably 0.8 to 5 wt% of 12-hydroxystearic acid; and
(b) a hydroxy functionalized solvent wherein the hydroxy functionalized solvent is methanol, ethanol, benzyl alcohol, 2-(2-ethoxyethoxy) ethanol, phenoxyethanol, pentylene glycol or a mixture thereof, the composition being substantially free of water, and the hydroxy functionalized solvent has an HD content of greater than 0.03.

Such a composition is typically substantially transparent. It is preferably free of crystallization and is preferably free of gelation. Without willing to be bound by theory, it is believed that the hydroxy-functionalysed solvent causes transparency in the context of the present invention, in 12-hydroxistearic acid comprising compositions which are substantially water free. Hence, the invention further relates to the use of a hydroxy functionalized solvent having an HD of greater than 0.03 to provide a substantially transparent composition being substantially free of water and comprising 12-hydroxystearic acid. Preferably, the composition of the invention, preferably such a substantially transparent composition, is a skin lightening composition.

The hydroxy functionalized solvent used in this invention will typically make up from 10% to 99.9999%, and preferably, from 15% to 85%, and most preferably, from 25% to 65% by weight of the total weight of the anhydrous composition, including all ranges subsumed therein.

Optional components suitable for use in the anhydrous composition of this invention may include co-solvents like mineral oils, plant based oils (e.g., sunflower, safflower, grape seed, rapeseed, Seabuckthorn, corn, olive, canola and/or avocado oil) silicone oils, synthetic or natural esters (including alkenyl or alkyl esters of fatty acids), or a mixture thereof. Amounts of these optional components may range from 0.0 to 75%, and preferably, from 0.3 to 70%, and most preferably, from 10 to 65% by weight of the anhydrous composition, including all ranges subsumed therein. When such co-solvents are optionally used, they are used with the proviso that the anhydrous composition remains at least substantially transparent, and preferably, transparent as described herein.

Silicone oils suitable for use may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, and preferably, from 4 to 5 silicon atoms.

Linear volatile silicone materials generally have viscosities of less than 5 centistokes at 25° C. while cyclic materials typically have viscosities of less than 10 centistokes.

Nonvolatile silicone oils useful as co-solvent material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from 5 to 100,000 centistokes at 25° C.

An often preferred silicone source is a cyclopentasiloxane (D5), dimethiconol solution or both.

Among suitable esters as co-solvents are:

(1) Alkenyl or alkyl esters of fatty acids having 10 to 20 carbon atoms like isopropyl palmitate, isopropyl isostearate, isononyl isonanonoate, oleyl myristate, isopropyl myristate, oleyl stearate, and oleyl oleate;

(2) Ether-esters such as fatty acid esters of ethoxylated fatty alcohols;

(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;

Anhydrous compositions comprising 12-hydroxystearic acid, mineral oil, sunflower oil, cyclopentasiloxane (and/or isopropyl palmitate) and hydroxy functionalized solvent are often desired.

Inclusion of hydrocarbons having a viscosity under 10 cps can be desired in the anhydrous compositions of this invention with isododecane being often preferred.

Use of the anhydrous composition of this invention to treat skin is often desired.

Additional skin benefit agents that may optionally be used with 12-hydroxystearic acid, in the skin benefit agents portion of the anhydrous composition of this invention include oil soluble actives like, petroselinic acid, rincinoleic acid, 9, 13-dihydroxy-12-ethoxy-10-octadecenoic acid, 9-hydroxy 10,12-octadecadienoic acid, octadecenedioic acid, Vitamin E (and its derivatives like tocopherol acetate), Vitamin A (retinol), Sepiwhite®, oil soluble sunscreens mixtures thereof or the like.

Such optional agents when used make up from 0.0001 to 10%, and preferably, from 0.001 to 8%, and most preferably, from 0.01 to 5% by weight of the anhydrous composition, including all ranges subsumed therein.

Fragrances, fixatives and abrasives may optionally be included in the anhydrous and water comprising compositions of the present invention. Each of these substances may range from 0.05 to 5%, preferably between 0.1 and 3% by weight.

Water soluble skin lightening actives like soybean extract, Vitamin C and its derivatives, Vitamin B and its derivatives (e.g. niacinamide or Vitamin B3) resorcinol (preferably, 4-ethyl, -butyl, -isopropyl, hexyl and/or phenylethyl resorcinol), Bowman Birk inhibitor, acetylglucosamine, calcium pantothenate, mixtures thereof or the like may be packaged with the anhydrous compositions of this invention but in a double phase product comprising water, or in concentrate or solid (including particulate or powder).

The water phase may optionally further include components like water soluble sunscreens, Vitamin B2, Vitamin B6, Folic Acid and Biotin. The total amount of such components making up the water phase as defined herein according to the present invention may range from 0.001 to 100%, and preferably, from 0.01% to 10%, optimally from 0.1 to 2.0% by weight of the total weight of the water phase, including all ranges subsumed therein.

Preservatives can desirably be incorporated into the separate and distinct phase comprising water of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, a variety of quaternary ammonium compounds, 1,2-octanediol, phenoxyethanol, ethylhexylglycerine as well as iodopropynyl butylcarbamate. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition, including all ranges subsumed therein.

Thickening agents may optionally be included in the hydrous phase of the double phase product. Cellulosics suitable for use include hydroxypropyl cellulose, hydroxypropyl methylcellulose, hydroxyethyl cellulose, ethylcellulose and sodium carboxy methylcellulose. Synthetic polymers are yet another class of effective thickening agent. This category includes crosslinked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Thickening agents suitable for use in the anhydrous phase of this invention include agents like Viscup P (Lonza), Versagel (Penreco) and trihydroxystearane.

Amounts of the thickener, when used, may range from 0.001 to 5%, and preferably, from 0.1 to 2%, and most preferably, from 0.2 to 0.5% by weight of the composition including all ranges subsumed therein.

Conventional humectants may be employed in the optional phase comprising water of the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.0 to 99.9%, preferably, between 25 and 50%, and preferably, from 25 to 50% by weight of such composition.

It is within the scope of this invention for the separate and distinct water containing phase to be an emulsion. The oils described herein are the often preferred oils wherein the preferred emulsifiers include those with an HLB of greater than 6 when an oil-in-water emulsion is preferred. Illustrative Examples of the types of emulsifiers suitable for use are described in U.S. Pat. No. 5,198,210, the disclosure of which is incorporated herein by reference.

The compositions of this invention may be made by mixing ingredients under conditions of moderate shear, temperature preferably between 70-85° C. and atmospheric temperature. No particular order of addition is required.

A wide variety of packaging can be employed to store and deliver the composition (including double phase product) of this invention. Packaging is often dependent upon the type of end-use. For instance, skin products generally employ plastic containers with an opening at a dispensing end covered by a closure. Typical closures are screw-caps, non-aerosol pumps and flip-top hinged lids. Packaging may involve a container with a roll-on ball on a dispensing end. Metallic cans pressurized by a propellant and having a spray nozzle serve as packaging for antiperspirants, shave creams and other personal care products. As previously noted, if a water phase is desired, the same may optionally be packaged separately and distinct from the anhydrous phase. Preferably the immiscible phases are packaged together as two distinct phases (i.e., biphasic).

The following examples are provided to facilitate an understanding of the present invention. The examples are not intended to limit the scope of the claims.

EXAMPLES

Examples (Nos. 1-91) represent formulations with a hydroxy functionalized solvent having a hydroxy group density (HD) over 0.03 in combination with 12-hydroxystearic acid that unexpectedly yield a substantially transparent or transparent composition. A "C" represents a substantially transparent or transparent composition for at least three (3) months after manufacturing (i.e., a composition consistent with this invention with no benefit agent crystallization or composition gelation) and an "X" represents an opaque (non-transparent, non-translucent) composition inconsistent with the claimed compositions of this invention and where benefit agent crystallization or composition gelation is almost immediately observed.

Examples 1-91

| SOLVENT | HD | 1% SBA/ 99% Solvent | 3% SBA/ 97% Solvent | 5% SBA/ 95% Solvent | 10% SBA/ 90% Solvent | 15% SBA/ 85% Solvent | 20% SBA/ 80% Solvent | 25% SBA/ 75% Solvent |
|---|---|---|---|---|---|---|---|---|
| Methanol | 0.53 | C | C | C | C | C | C | X |
| Ethanol | 0.37 | C | C | C | C | C | X | X |
| Benzyl Alcohol | 0.16 | C | C | C | X | X | X | X |
| 2-(2-Ethoxyethoxy)ethanol | 0.13 | C | C | C | X | X | X | X |
| Pehnoxyethanol | 0.12 | C | C | C | X | X | X | X |
| Isostearyl Alcohol | 0.06 | C | C | X | X | X | X | X |
| Octyldodecanol | 0.06 | C | C | X | X | X | X | X |
| Conjugated Linoleic Acid | 0.06 | C | C | X | X | X | X | X |
| Isostearic Acid | 0.06 | C | C | X | X | X | X | X |
| Ethylhexyl Hydroxystearate | 0.04 | C | X | X | X | X | X | X |
| Propylene Glycol | 0.45 | C | X | X | X | X | X | X |
| Butylene Glycol | 0.38 | C | X | X | X | X | X | X |
| Pentylene Glycol | 0.33 | C | C | C | C | X | X | X |

SBA = Skin benefit agent, 12-hydroxystearic acid

Examples 92-93

| INGREDIENT | % | % |
|---|---|---|
| Mineral Oil 70 Sus | 14 | 14 |
| Isopropyl Palmitate | 50 | 83 |
| Sunflower Seed Oil | 1 | 1 |
| Cyclopentasiloxane | 1 | 1 |
| Isostearyl Alcohol | 33 | 0 |
| 12-hydroxystearic acid | 1 | 1 |
| Total | 100 | 100 |

The Samples in Example 92-93 were made by mixing the ingredients with moderate shear at 80° C. and under atmospheric pressure. The sample of Example 92, comprising functionalized solvent consistent with this invention (e.g., isostearyl alcohol), unexpectedly remained transparent for more than three months after manufacturing. In contrast, the Sample of Example 93, deplete of hydroxy functionalized solvent as claimed in this invention, crystallized and gelled almost immediately after making whereby the composition was not suitable for topical application. The Sample made in Example 92 was topically applied to trained panelists, all of whom concluded the composition yielded excellent sensory and skin quality benefits immediately after application.

Examples 94-102

The Samples of Examples 94-102 were made in a manner similar to the one described for Examples 92 to 93.

| INGREDIENT | % | % | % | % | % | % | % | % | % |
|---|---|---|---|---|---|---|---|---|---|
| Mineral Oil 70 Sus | 14 | 14 | 14 | 5 | 85 | | | 66 | 14 |
| Isopropyl Palmitate | 50 | 83 | 50 | 10 | 10 | | | | 50 |
| Sunflower Seed Oil | 1 | 1 | 1 | 1 | | 66 | | | 1 |
| Cyclopentasiloxane | 1 | 1 | 1 | 1 | | | 66 | | 1 |
| Isostearyl Alcohol | 33 | | | 80 | | 33 | 33 | 33 | |
| Phenoxyethanol | | | 33 | | | | | | |
| Cetyl Alcohol (solid) | | | | | | | | | 33 |
| 12-hydroxystearic acid | 1 | 1 | 1 | 3 | 3 | 1 | 1 | 1 | 1 |
| Total | 100 | 100 | 100 | 100 | 100 | 100 | 100 | 100 | 100 |

Samples having hydroxy functionalized solvent consistent with this invention unexpectedly remained clear/transparent for more than three months after manufacturing. Samples from Examples 95, 98 and 102, deplete of hydroxy functionalized solvent as claimed in this invention, crystallized and gelled almost immediately after being made. These gelled compositions were not desirable nor suitable for topical application. When Samples from Examples 94, 96, 97, 99, 100, 101 were applied topically to skin, all trained panelists concluded that the compositions yielded excellent sensory benefits immediately after application. The panelists also concluded a light and natural sensory profile was detected after application along with a general improvement in skin quality.

The invention claimed is:

1. A composition comprising:
   (a) 0.01 to 20 wt% of 12-hydroxystearic acid; and
   (b) a hydroxy functionalized solvent, the hydroxy functionalized solvent comprising methanol, ethanol, benzyl alcohol, 2-(2-ethoxyethoxy) ethanol, phenoxyethanol, isostearyl alcohol, octyldodecanol, pentylene glycol or a mixture thereof, the composition being substantially free of water, the hydroxy functionalized solvent has an hydroxy group density content of greater than 0.03, and the hydroxy functionalized solvent makes up from 15% to 85% by weight of the composition, the composition being free of gelation and crystallization with a viscosity from 10 to 4,000 cps.

2. The composition according to claim 1, wherein the composition is substantially transparent.

3. The composition according to claim 1 wherein the composition further comprises a co-solvent miscible with the hydroxy functionalized solvent.

4. The composition according to claim 3 wherein the hydroxy functionalized solvent is pentylene glycol, ethanol, methanol or a mixture thereof.

5. The composition according to claim 1 wherein the composition is transparent.

6. The composition according to claim 1 wherein the composition further comprises a co-solvent which is an ester, silicone oil, mineral oil, plant based oil or a mixture thereof.

7. The composition according to claim 6 wherein the ester is the co-solvent and the co-solvent is isopropyl palmitate, isopropyl isostearate, isononyl isonanonate, oleyl myristate, isopropyl myristate, oleyl stearate, oleyl oleate or mixture thereof.

8. The composition according to claim 7 wherein the co-solvent is isopropyl palmitate.

9. The composition according to claim 1 wherein the composition further comprises petroselinic acid, ricinoleic acid, 9,13-dihydroxy-12-ethoxy-10-octadecenoic, 9-hydroxy, 10,12-octadecadenoic acid, Vitamin E, Vitamin A, an oil soluble sunscreen or a mixture thereof.

10. The composition according to claim 1 packaged with a separate and distinct water phase.

11. A method for treating skin by topically applying the composition of claim 1 to skin, to moisten the skin, strengthen the stratum corneum, provide anti-aging benefits to the skin and/or lightens the skin.

12. The composition according to claim 1 wherein the composition comprises 0.8 to 5% by weight 12-hydroxystearic acid, and isostearyl alcohol or octyldodecanol.

13. the composition according to claim 12 wherein the composition is transparent.

14. The composition according to claim 1 when the composition further comprises hexyl resorcinol.

* * * * *